(12) United States Patent
Woo et al.

(10) Patent No.: US 9,028,432 B2
(45) Date of Patent: May 12, 2015

(54) FOOTWORK TRAINING SYSTEM AND METHOD

(75) Inventors: Helen Woo, Hillsboro, OR (US); Allan M. Schrock, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 364 days.

(21) Appl. No.: 13/440,553

(22) Filed: Apr. 5, 2012

(65) Prior Publication Data
US 2012/0191229 A1   Jul. 26, 2012

Related U.S. Application Data

(63) Continuation of application No. 11/737,571, filed on Apr. 19, 2007.

(51) Int. Cl.
*A61B 5/11* (2006.01)
*A61B 5/00* (2006.01)
(Continued)

(52) U.S. Cl.
CPC .............. *A61B 5/112* (2013.01); *A61B 5/0002* (2013.01); *A61B 5/1122* (2013.01); *A61B 5/6805* (2013.01); *A61B 5/6807* (2013.01); *A61B 5/681* (2013.01); *A61B 5/6814* (2013.01); *A61B 5/6816* (2013.01); *A61B 5/6828* (2013.01); *A61B 5/6892* (2013.01); *A61B 2562/0219* (2013.01); *A61B 2562/0247* (2013.01); *A61B 2562/046* (2013.01); *A63B 6/00* (2013.01); *A63B 24/0006* (2013.01); *A63B 24/0062* (2013.01); *A63B 24/0084* (2013.01); *A63B 2024/0012* (2013.01); *A63B 2024/0068* (2013.01); *A63B 2024/0081* (2013.01); *A63B 2071/0625* (2013.01); *A63B 2071/063* (2013.01); *A63B 2071/065* (2013.01); *A63B 2071/068* (2013.01);

(Continued)

(58) Field of Classification Search
CPC ............... A63B 2024/0003; A63B 2024/0006; A63B 2024/0009; A63B 2024/0012; A63B 2024/0015
USPC .......... 600/587, 592, 595; 434/247, 250, 255; 482/8, 9; 463/4, 8
See application file for complete search history.

(56) References Cited

U.S. PATENT DOCUMENTS

| | | | |
|---|---|---|---|
| 4,571,680 | A | 2/1986 | Wu |
| 4,776,323 | A | 10/1988 | Spector |

(Continued)

FOREIGN PATENT DOCUMENTS

| | | |
|---|---|---|
| WO | 8703498 | 6/1987 |
| WO | 2006103676 | 10/2006 |

OTHER PUBLICATIONS

Extended European Search Report dated Apr. 25, 2013 in European Patent Application No. EP 08 73 2090.

(Continued)

*Primary Examiner* — Adam Eiseman
(74) *Attorney, Agent, or Firm* — Plumsea Law Group, LLC

(57) ABSTRACT

A system and method for evaluating an activity includes an article of clothing provided with a sensor capable of detecting the impact of the article of clothing, such as a shoe, on a surface. A system receives and interprets the pattern of impacts made during the performance of the activity. The system compares these impacts with those of a target routine. Iterations of the same performance may be stored in the system so that ongoing progress may be measured. The system may be used to enhance class teaching, in the home, or for Internet competition. The activity may include dance, yoga, martial arts, or similar activities.

9 Claims, 17 Drawing Sheets

(51) Int. Cl.
*A63B 24/00* (2006.01)
*A63B 6/00* (2006.01)
*A63B 71/06* (2006.01)

(52) U.S. Cl.
CPC ..... *A63B 2220/803* (2013.01); *A63B 2220/836* (2013.01); *A63B 2225/20* (2013.01); *A63B 2225/50* (2013.01); *A63B 2244/22* (2013.01)

(56) References Cited

U.S. PATENT DOCUMENTS

| | | | |
|---|---|---|---|
| 5,461,188 A | 10/1995 | Drago et al. | |
| 5,714,706 A | 2/1998 | Nakada et al. | |
| 5,765,300 A | 6/1998 | Kianka | |
| 5,855,080 A | 1/1999 | Van Staden | |
| 6,315,571 B1 | 11/2001 | Lee | |
| 6,336,891 B1 | 1/2002 | Fedrigon et al. | |
| 6,639,140 B2 | 10/2003 | Mishima | |
| 6,685,480 B2 | 2/2004 | Nishimoto et al. | |
| 6,716,139 B1 | 4/2004 | Hosseinzadeh-Dolkhani et al. | |
| 6,867,361 B2 | 3/2005 | Nishitani et al. | |
| 6,991,586 B2 | 1/2006 | Lapcevic | |
| 7,003,122 B2 | 2/2006 | Chen | |
| 7,492,268 B2 * | 2/2009 | Ferguson et al. | 340/573.1 |
| 7,627,451 B2 * | 12/2009 | Vock et al. | 702/178 |
| 7,670,263 B2 * | 3/2010 | Ellis et al. | 482/8 |
| 7,927,253 B2 * | 4/2011 | Vincent et al. | 482/9 |
| 2005/0233859 A1 | 10/2005 | Takai et al. | |
| 2006/0022833 A1 | 2/2006 | Ferguson et al. | |
| 2006/0136173 A1 * | 6/2006 | Case et al. | 702/182 |
| 2007/0021269 A1 | 1/2007 | Shum | |
| 2007/0123391 A1 | 5/2007 | Shin et al. | |
| 2007/0231778 A1 * | 10/2007 | Kim et al. | 434/250 |
| 2008/0258921 A1 | 10/2008 | Woo et al. | |

OTHER PUBLICATIONS

International Search Report and Written Opinion, mailed Aug. 11, 2008, from PCT Application No. PCT/US2008/056786.
Office Action mailed Jun. 23, 2014 for U.S. Appl. No. 11/737,571.

* cited by examiner

FIG. 9

| BEAT | A | | B | | RESULT |
|---|---|---|---|---|---|
| | L | R | L | R | |
| ♩1 | | X | | X | FOOT FALL: CORRECT |
| | | | | | TIMING: LATE |
| ♩2 | X | | | | |
| ♩3 | X | X | | | |
| ♩4 | | X | | | |

FIG. 10

| BEAT | A | | B | | RESULT |
|---|---|---|---|---|---|
| | L | R | L | R | |
| ♩1 | | X | | X | FOOT FALL: CORRECT |
| | | | | | TIMING: LATE |
| ♩2 | X | | X | X | FOOT FALL: INCORRECT |
| | | | | | TIMING: CORRECT |
| ♩3 | X | X | | | |
| ♩4 | | X | | | |

FIG. 11

| BEAT | A | | B | | RESULT |
|---|---|---|---|---|---|
| | L | R | L | R | |
| ♩1 | | X | | X | FOOT FALL: CORRECT |
| | | | | | TIMING: LATE |
| ♩2 | X | | X | X | FOOT FALL: INCORRECT |
| | | | | | TIMING: CORRECT |
| ♩3 | X | X | X | X | FOOT FALL: CORRECT |
| | | | | | TIMING: CORRECT |
| ♩4 | | X | | | |

FIG. 12

| BEAT | A | | B | | RESULT |
|---|---|---|---|---|---|
| | L | R | L | R | |
| ♩1 | | X | | X | FOOT FALL: CORRECT |
| | | | | | TIMING: LATE |
| ♩2 | X | | X | X | FOOT FALL: INCORRECT |
| | | | | | TIMING: CORRECT |
| ♩3 | X | X | X | X | FOOT FALL: CORRECT |
| | | | | | TIMING: CORRECT |
| ♩4 | | X | | X | FOOT FALL: CORRECT |
| | | | | | TIMING: EARLY |

SUMMARY

CURRENT

CORRECT FOOTFALLS
3/4
75%

CORRECT TIMING
2/4
50%

PREVIOUS

NO PREVIOUS
ROUTINE SAVED

| BEAT | A L | A R | B L | B R | RESULT |
|---|---|---|---|---|---|
| ♩1 | | X | | X | FOOT FALL: CORRECT / TIMING: CORRECT |
| ♩2 | X | | | | |
| ♩3 | X | X | | | |
| ♩4 | | X | | | |

FIG. 17

| BEAT | A L | A R | B L | B R | RESULT |
|---|---|---|---|---|---|
| ♩1 | | X | | X | FOOT FALL: CORRECT / TIMING: CORRECT |
| ♩2 | X | | X | | FOOT FALL: CORRECT / TIMING: CORRECT |
| ♩3 | X | X | | | |
| ♩4 | | X | | | |

FIG. 18

| BEAT | A L | A R | B L | B R | RESULT |
|---|---|---|---|---|---|
| ♩1 | | X | | X | FOOT FALL: CORRECT / TIMING: CORRECT |
| ♩2 | X | | X | | FOOT FALL: CORRECT / TIMING: CORRECT |
| ♩3 | X | X | X | X | FOOT FALL: CORRECT / TIMING: CORRECT |
| ♩4 | | X | | | |

FIG. 19

| BEAT | A L | A R | B L | B R | RESULT |
|---|---|---|---|---|---|
| ♩1 | | X | | X | FOOT FALL: CORRECT / TIMING: CORRECT |
| ♩2 | X | | X | | FOOT FALL: CORRECT / TIMING: CORRECT |
| ♩3 | X | X | X | X | FOOT FALL: CORRECT / TIMING: CORRECT |
| ♩4 | | X | | X | FOOT FALL: CORRECT / TIMING: LATE |

SUMMARY

CURRENT

CORRECT FOOTFALLS
4/4
100%

CORRECT TIMING
3/4
75%

PREVIOUS

IMPROVED FOOTFALL
IMPROVED TIMING

FIG. 20

FOOTWORK TRAINING SYSTEM AND METHOD

CROSS-REFERENCE TO RELATED APPLICATION

This application is a continuation of U.S. Patent Publication Number 2012/0191229, currently U.S. application Ser. No. 11/737,571, entitled "Footwork Training System and Method", filed on Apr. 19, 2007, and allowed on Jan. 15, 2015, which application Publication is hereby incorporated by reference in its entirety.

BACKGROUND OF THE INVENTION

1. Field of the Invention

The present invention relates generally to a system and method for teaching and evaluating footwork routines. More particularly, the invention relates to footwear with a sensor system in communication with an evaluation processor to generate feedback regarding footstrike patterns.

2. Description of Related Art

Home systems for personal training and fitness have become increasingly popular, especially in learning new activities and techniques. For example, video and DVD training systems for activities ranging from dancing to yoga are readily available from any retail video or DVD outlet. These systems teach basic postures and movements, often by showing an expert practitioner perform the routine slowly and then at speed.

Similarly, in live classes for physical activities, typically a single instructor teaches a group of students the proper positions and movements for the activity. Visual aids are often provided to assist the instructor in demonstrating footwork routines. For example, footwork charts for standard foot placement and position changes in ballroom dance have long been used to reinforce live demonstration of the movements. However, whether learned in the privacy of a home or in a studio with a group, students may not have access to an instructor to review the student's movements at all times during a routine. Therefore, the student and the teacher may find determining whether a student is performing each step in the routine appropriately difficult. With at-home study, instructor feedback is an unavailable luxury. Additionally, the motivation provided by an enthusiastic instructor is also unavailable to users of at-home systems.

Several systems have been developed to provide cues to a user during the performance of a routine involving body movements. For example, the Nike+iPod Sport Kit wirelessly links a sensor placed in an article of athletic footwear, a Nike® running shoe, with a music player, an Apple iPod®. The processor in the iPod gathers footstrike information from the sensor in the article of footwear and uses that information to generate statistics regarding the runner's workout, such as distance and calories burned. Optionally, the iPod generates spoken feedback regarding the progress of the workout, for example a voice may be generated giving the time elapsed, distance run, calories burned, or similar statistics.

However, none of these systems provides real-time evaluation of a user's footwork performance compared to a baseline target performance. Additionally, none of these systems teaches using ongoing comparisons to help the user to evaluate his or her progress in learning the target performance.

Therefore, there exists a need in the art for a system and method for automated evaluation of activities which involve precise timing and positioning, such as dancing, martial arts, and yoga.

SUMMARY OF THE INVENTION

In one aspect, the invention provides a system for evaluating a performance of an activity where a portion of a user's body impacts a surface comprising: an article of clothing sized and dimensioned to fit the portion of the user's body, a sensor attached to the article of clothing, the sensor being capable of detecting an impact of the article of clothing against the surface, a processor connected to the sensor via a communication link, a target impact pattern accessible by the processor, and a display.

In another aspect, the article of clothing comprises an article of footwear.

In another aspect, the article of footwear is a shoe.
In another aspect, the article of clothing is a torso covering.
In another aspect, the article of clothing is a leg covering.
In another aspect, the article of clothing is a band.
In another aspect, the article of clothing is jewelry.
In another aspect, the communication link is a wireless connection.
In another aspect, the communication link is a wireline link.
In another aspect, the processor is a computer.
In another aspect, the display is a computer monitor or screen.
In another aspect, the processor is a portable electronic device.
In another aspect, the portable electronic device is a personal digital assistant.
In another aspect, the portable electronic device is an audio-visual player.
In another aspect, the processor is a video game console.

In another aspect, the invention provides a method for evaluating an activity where a portion of a user's body impacts a surface comprising the steps of: (i) providing a target impact pattern to an evaluation system; (ii) the user performing the activity wearing an article of clothing on the portion of the user's body, the article of clothing incorporating a sensor capable of detecting a performance impact pattern generated by the user; (iii) communicating the performance impact pattern to the evaluation system; and (iv) comparing the performance impact pattern to the target impact pattern.

In another aspect, the article of clothing comprises a shoe.
In another aspect, step (iii) of the method comprises transmitting the performance impact pattern to the evaluation system via a wireless communication link.
In another aspect, step (iii) of the method comprises connecting the article of clothing to the evaluation system with a wireline communication link.
In another aspect, the method comprises the step of: (v) determining a performance metric based upon step (iv).
In another aspect, the method further comprises the step of: (vi) displaying a visual representation of the performance impact pattern and the performance metric.
In another aspect, the method further comprises the step of: (vi) displaying the target impact pattern.
In another aspect, the method further comprises the step of: (v) storing the performance impact pattern.
In another aspect, the method further comprises the steps of: (vii) determining a first performance metric based upon step (iv); (viii) repeating the activity at least once to generate a new performance pattern; (ix) comparing the new performance pattern to the target pattern to determine a new performance metric; and (x) comparing the new performance metric to the first performance metric to determine a progress metric.

In another aspect, the method further comprises the step of: (xi) displaying at least one of the performance pattern, the new performance pattern, the target pattern, the first performance metric, and the new performance metric.

In another aspect, the activity comprises a performance of at least one of a dance, a yoga posture, a boxing move, and a martial arts movement.

In another aspect, the steps are performed in a class.

In another aspect, the steps are performed in a home.

In another aspect, the invention provides a system for evaluating a performance of an activity where a portion of a user's body impacts a surface comprising a sensor attachable to the portion of the user's body, the sensor being capable of detecting an impact of the portion of the user's body against the surface, a processor connected to the sensor via a communication link, a memory module accessible by the processor, a target impact pattern accessible by the processor, and a display connected to the processor.

In another aspect, the system includes an input device.

In another aspect, the input device is an optical drive.

In another aspect, the input device is a magnetic drive.

In another aspect, the input device is a keypad.

In another aspect, the input device is a microphone.

In another aspect, the processor and the input device are disposed within a housing.

In another aspect, the system includes an external communications device connecting the processor to an external communications network.

In another aspect, the external communications device is a modem.

In another aspect, the external communications network is the Internet.

In another aspect, a first sensor is positioned on the user and a second sensor is positioned on a mat, wherein the mat is communicatively connected to the processor.

In another aspect, the mat incorporates a plurality of sensors.

In another aspect, the mat has multiple layers.

Other systems, methods, features and advantages of the invention will be, or will become, apparent to one of ordinary skill in the art upon examination of the following figures and detailed description. It is intended that all such additional systems, methods, features and advantages be included within this description and this summary, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

FIGS. 9-12 are screen shots of an embodiment of a visual representation of a system displaying the dance steps of the dancers shown in FIG. 8 and evaluating the second dancer;

FIG. 13 is a screen shot of a summary screen showing statistics regarding a user's performance;

FIGS. 16-19 are screen shots of an embodiment of a visual representation of a system displaying the dance steps of the dancers shown in FIG. 4 and evaluating the second dancer;

FIG. 20 is a screen shot of a summary screen showing statistics regarding a user's performance;

DETAILED DESCRIPTION OF THE PREFERRED EMBODIMENTS

Figure 1:
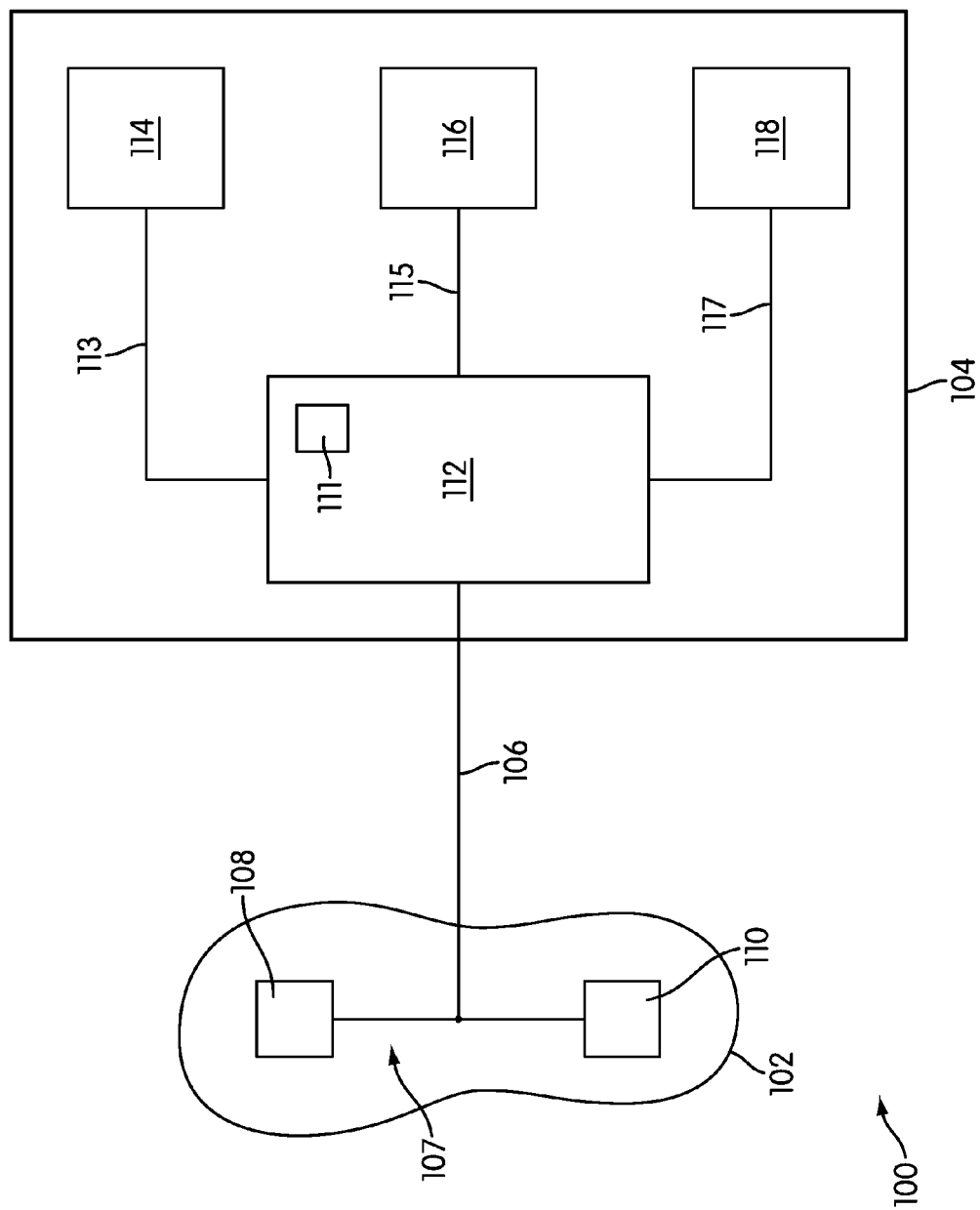
FIG. 1 is a schematic drawing of an embodiment of an evaluation system according to the invention.

A system and method for evaluating a performed routine involving footwork is provided. Generally, the system utilizes a sensor-rich article of footwear (also referred to as "sensor article" or "article"). FIG. 1 is a schematic view of an embodiment of a system 100 for evaluating a footstrike pattern generated by a user (not shown). In this embodiment, an article of footwear 102 including a sensor system 107 is linked to an evaluation module 104. Article of footwear 102 may be any type of footwear, such as an athletic shoe, a sandal, a dance shoe, or the like, capable of having a being adapted to include sensor system 107. Sensor system 107 may be integrated into article of footwear 102, such as being embedded within a sole of article of footwear 102.

Figure 2:
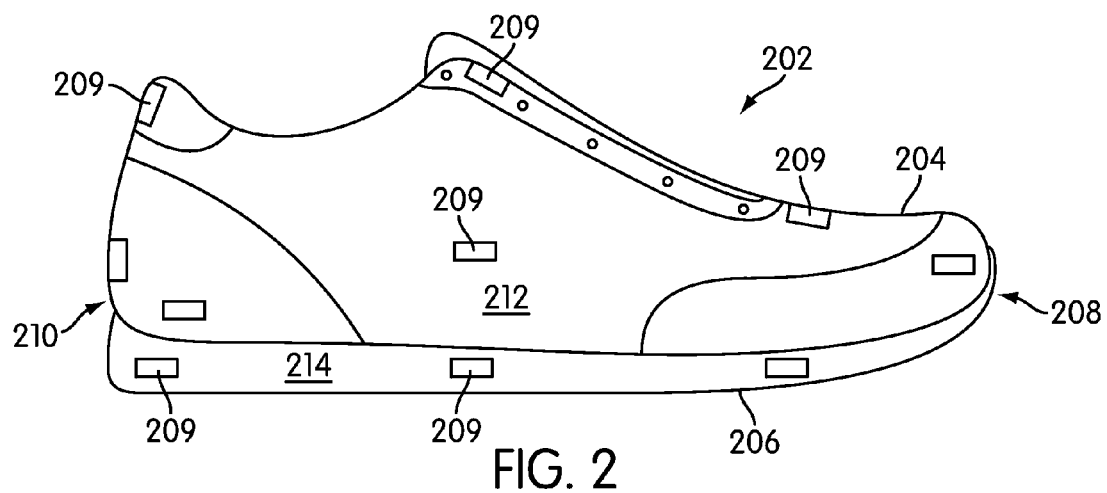
FIG. 2 is a schematic side view of an embodiment of a sensor-rich article of footwear showing possible locations of sensors.
Figure 3:
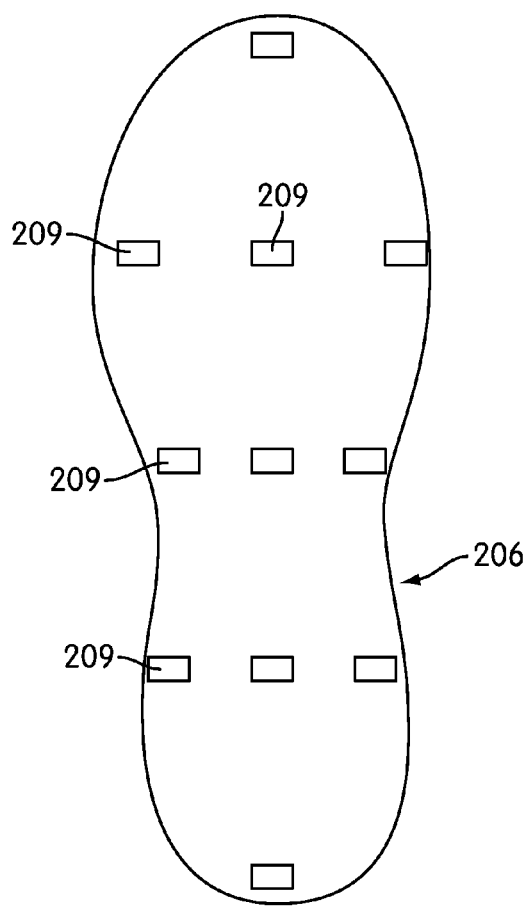
FIG. 3 is a schematic plan view of a sole of an embodiment of a sensor-rich article of footwear showing possible locations of sensors.

FIGS. 2 and 3 show various possible and optional locations for sensors on articles of footwear. FIG. 2 is a side view of an upper 204 attached to a sole 206. Sensors 209 may be positioned anywhere on upper 204, such as in a forefoot region 208, a heel region 210, and/or a medial or lateral sidewall 212. Sensors 209 may also be positioned on a sidewall 214 of sole 206. FIG. 3 shows additional locations for the placement of sensors 209 on the bottom or ground-engaging surface of sole 206. In another embodiment, the entirety of sole 206 may be made from sensor 209 or an array of sensors 209. It will be appreciated that any of sensors 209 may be used or not used in any embodiment. For example, in one embodiment, sensor 209 may be provided in only one article of footwear 202, while in another embodiment, sensor 209 is provided in two articles of footwear 202. Many different combinations of the number of sensors 209 provided and their locations are contemplated, depending upon such factors as the ability to determine body alignment, the power consumed, the ease of using the system, the desired precision provided by the sensor system, etc.

In another embodiment, sensor system 107 may be detachable from article of footwear 102. For example, in one embodiment, sensor system 107 is a sensor-rich disk removably attachable to article of footwear 102, such as by tying sensor system 107 to laces of article of footwear 102 or placing the disk into a slot or space provided within article of footwear 102.

Sensor system 107 may include any type of sensor capable of detecting a footstrike, such as a pressure sensor, an accelerometer, a proximity sensor, an RF tag, or the like. While one or more sensors positioned at any location on article of footwear 102 may be provided with sensor system 107, preferably sensor system 107 includes at least forefoot sensor 108 and heel sensor 110 so that forefoot movements may be detected separately from heel movements.

Figure 4:
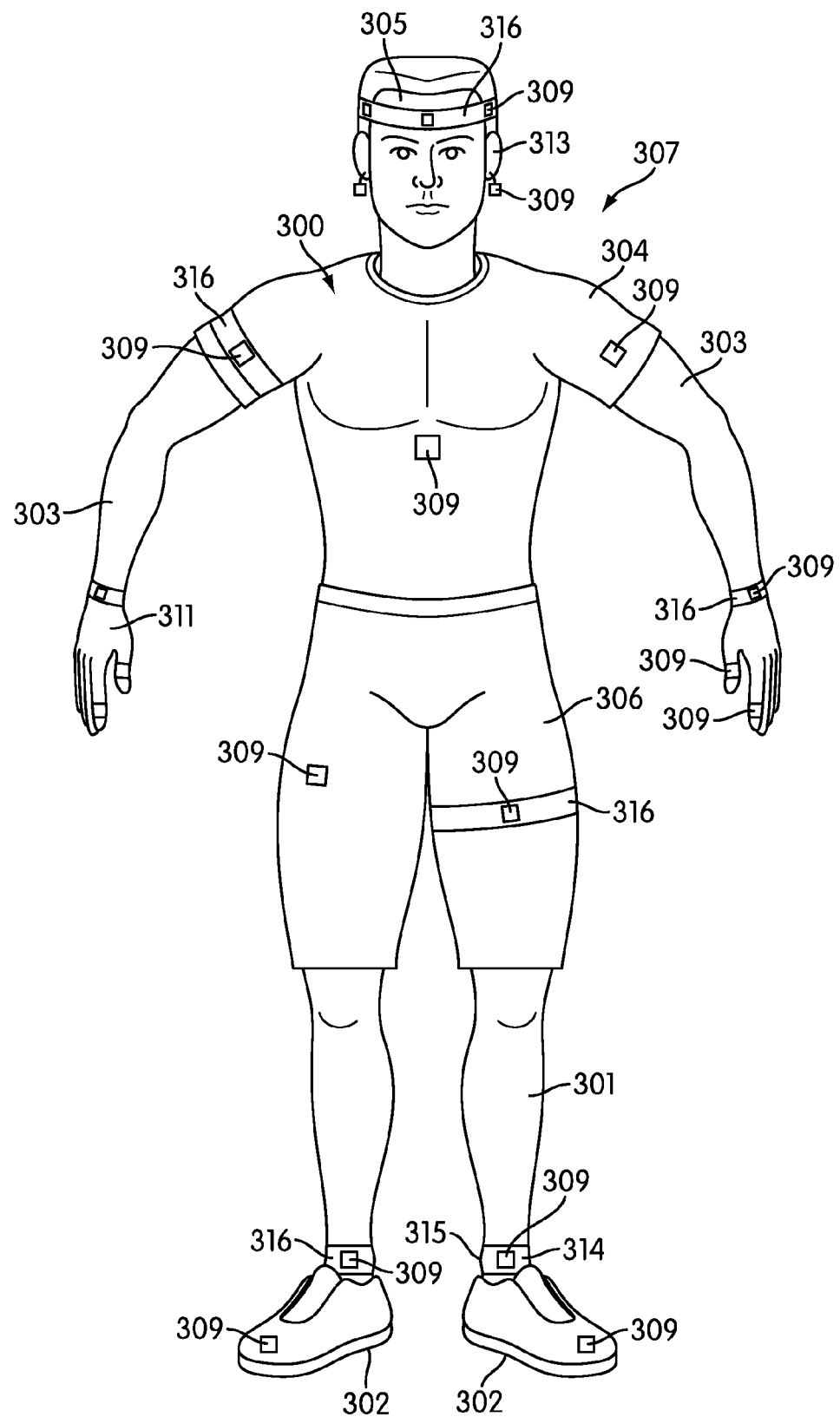
FIG. 4 is a schematic view of a person wearing sensor-rich articles showing possible locations of sensors.

Various articles of footwear incorporating sensor systems able to register footstrikes are known in the art, such as those described in U.S. patent publication number US 2005/0126370 and U.S. Pat. Nos. 6,867,361 and 6,639,140. Any such article of footwear may be incorporated in system 100. In another embodiment, additional articles of clothing may include sensors linked to system 100, such as gloves for indicating handstrikes, for use with activities such as yoga, boxing, martial arts, and/or couples dancing where the hands may impact a surface, such as a mat, dummy, bag, or other hands. FIG. 4 shows various possible but non-exclusive locations on an athlete's body 300 for the placement of sensors 309 that allow the alignment of the feet, legs, torso, head and arms to be determined and evaluated. Sensors 309 may be permanently or removably affixed directly to an article of clothing or footwear. For example, a sensor 309 may be stitched or adhered to pants 306, shirt 304, or sock cuff 314.

Alternatively, sensors 309 may be attached to a band 316 that can encircle an appendage of body 300. Band 316 may be a unitary or monolithic encircling member made from an elastic material, such as known wristbands or headbands. Alternatively, band 316 may be made from a non-elastic material with free ends configured to be attached to each other using any known fastening system, such as a buckle, a snap, a button, or a hook-and-loop closure. Band 316 is preferably sized and dimensioned to fit a particular appendage. For example, band 316 head 305 is preferably larger than band 316 on arm 303 but smaller than band 316 on leg 306.

Alternatively, sensors 309 may be attached directly to body 300. This attachment may be similar to attaching jewelry, such as an earring or ear cuff on ear 313 or a ring on hand 311. Similarly, sensors 309 may be provided with an adhesive backing so that sensors 309 may be directly attached to body 300. Sensor 309 may also be provided with a decorative cover for aesthetic purposes. For example, a dancer with a sensor on his or her head may choose a design to mimic the look of a bindi for an Indian dance or a tattoo or jewel for a traditional Indonesian dance. Alternatively, an athlete using a sensor in a competition may wish to sport a school or corporate sponsorship logo on the sensor.

Referring again to FIG. 1, sensor system 107 is connected to evaluation module 104 via a communication link 106. Communication link 106 may be any type of communications link known in the art capable of transmitting the information generated by sensor system 107 to evaluation module 104. For example, communication link 106 may be a wireline link. In one embodiment, communication link 106 is a conventional cable, such as a coaxial cable electrically connected to sensor system and evaluation module 104. In another embodiment, communication link 106 is an optical cable optically connected to sensor system 107 and evaluation module 104. In another embodiment, communication link 106 is a wireless link, such as an RF or infrared link. In such an embodiment, sensor system 107 includes a transmitter or transceiver which transmits the information generated by sensor system 107 to evaluation module 104 using any protocol known in the art, such as Bluetooth.

Evaluation module 104 preferably includes a processor 112 linked to a memory module 114. Processor 112 may be any type of processor known in the art, such as a computer, video game console, portable digital assistant (PDA), portable audio-visual player, such as an MP3 player or iPod®, a processing chip, or the like. Processor 112 is used to gather and analyze the footstrike information generated by sensor system 107. Processor 112 preferably includes a clock or timing circuit 111 so that processor 112 is able to track rhythms, beats, or counts.

Memory module 114 is any type of memory, such as magnetic memory, optical, or flash memory. In one embodiment, memory module 114 includes rewritable memory and read-only memory (ROM). In another embodiment, memory module 114 includes only ROM. Memory module 114 is preferably used to store footstrike information, such as target patterns and historical data generated by sensor system 107.

Evaluation module 104 also preferably includes an input device 116 to allow a user to communicate with processor 102 and/or memory module 114. Preferably input device 116 includes a receiver and/or transmitter for communicating with article of footwear 102. In one embodiment, input device 116 is able only to receive information from article of footwear 102. In another embodiment, input device 116 may also allow processor 102 and/or memory module 114 to transmit information to article of footwear 102, such as software updates. For example, a user may wish to associate a date or an identifier with a routine of footstrikes. Input device 116 may be any known type of input device, such as a keyboard, a disk drive, a mouse or equivalent device, a microphone for vocal inputs, combinations of these devices, or the like. Preferably, drivers for input device 116 are stored on memory module 114, for example voice recognition software for a microphone or software drivers for a keyboard.

Evaluation module 104 also preferably includes a display 118. Display 118 may be any type of display which is capable of providing audio and/or visual cues to the user. Preferably, display 118 is an audio-visual device such as a monitor or integrated computer screen, a television, or a screen on a portable audio-visual player. Display 118 may also be a projector, a stereo, or the like. Display 118 is used to provide the evaluation information generated by processor 112 to the user.

Preferably, all of the individual components of evaluation module 104 are linked to processor 112 so that processor 112 may control the usage of these components. For example, in this embodiment, memory module 114 is linked to processor 112 via first link 113, input device 116 is linked to processor 112 via a second link 115, and display 118 is linked to processor 112 via a third link 117. Links 113, 115, 117 may be any type of electrical or optical communications link known in the art capable of transmitting information from a processor to a component, such as an electrical cable, an optical cable, a printed circuit link, or a wireless signal.

In one embodiment, each component of evaluation module 104 is provided as a separate component. For example, processor 112 may be the processing chip of a central processing unit of a desktop computer, memory module 114 may be an external flash drive, input device 116 may be a keyboard, and display 118 may be a monitor. In another embodiment, all components of evaluation module 104 are integrated. For example, evaluation module 104 may be a laptop computer. In such an embodiment, processor 112 may be an internal processing chip, memory module 114 may be an internal hard drive, input device 116 is an integrated keyboard and mouse, and display 118 may be an integrated In general operation, a user dons article of footwear 102 and performs a routine. Sensor system 107 detects any impacts of article of footwear 102 against a surface such as a floor. The information detected by sensor system 107 is transmitted to evaluation module 104 via communications link 106. Processor 112 receives the information, interprets the information, and organizes the raw data into a useful form, such as a database. Processor 112 recalls from memory module 114 a target impact pattern and compares the information gathered from sensor system 107 with the target impact pattern. Processor 112 then generates a visual and/or audio summary of the detected pattern and the evaluation. The usage of system 100 is described greater detail below.

Figure 5:
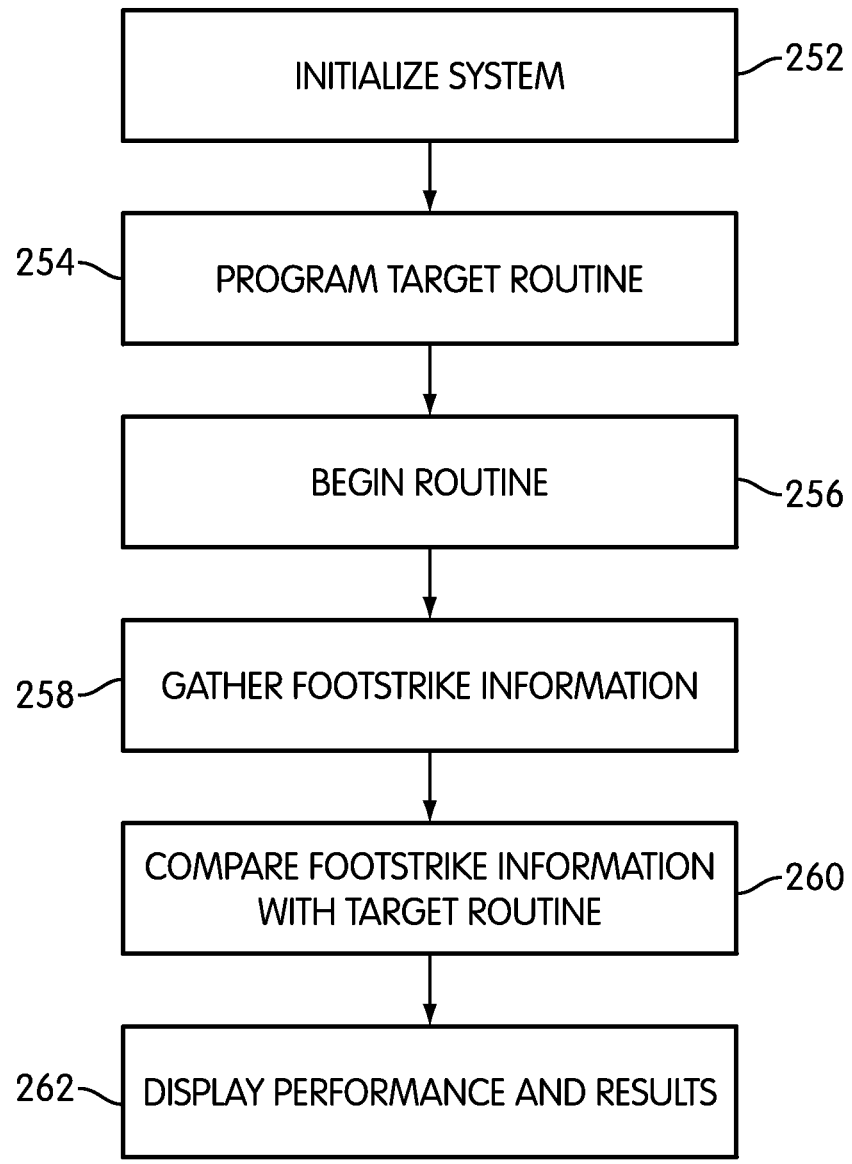
FIG. 5 is a flowchart of an embodiment of a method of evaluating a footstrike routine according to the invention.

FIG. 5 shows an embodiment of a method 250 to evaluate a footwork-based activity incorporating a system such as system 100. The footwork-based activity may be any type of activity where footstrikes may be detected, such as aerobic exercises, yoga, dancing, and the like. Preferably, the footwork-based activity is an activity where both timing and foot position are characteristics of the activity, such as dancing. For the purposes of simplicity and clarity, the following discussion refers to the activity as dancing, however any footwork-based activity as described above is contemplated.

In step 252 of evaluation method 250 as shown in FIG. 2, the user or users initialize an evaluation system, such as system 100 shown in FIG. 1. To initialize system, the user or users whose footstrikes are to be evaluated don footwear such as footwear 102 and power or turn on system evaluation module 104. In step 254 of method 250, a target routine is programmed or otherwise loaded into memory module 114, such as from a disk or video game cartridge. The target routine is preferably stored in a database or similar organized data structure mapping a series of footstrikes. In another embodiment, a user wearing sensor-filled article of footwear 102 may perform a routine. The footstrikes of the routine are detected by sensor system 107 and transmitted to evaluation module 104 and stored in memory module 114. The footstrikes may be full foot impacts, or separated into zones, so that a location of the foot impacting a surface may be included. For example, it may be desired that a toe drag across a surface or a heel strike a surface while the rest of the foot does not make contact with the surface.

In step 256, the user to be evaluated begins to perform his or her footstrike routine, impacting a surface such as a floor with article of footwear 102. Sensor system 107 detects these footstrikes. In step 258, the footstrike information is gathered by evaluation module 104. For example, sensor system 107 may transmit the footstrike information to evaluation module 104 where the information is received by processor 102. Processor 102 identifies the type of footstrike, such as a right foot impact, a left foot impact, a sliding of the foot, or the like. Processor 102 also determines the timing of the footstrikes, such as by time stamping the received footstrikes according to a clock or timing circuit connected to processor 102. Processor 102 preferably assembles this information into a database or organized data structure comparable to the data structure storing the footstrike information for the target routine. This footstrike information is then preferably stored in memory module 114.

Figure 7:
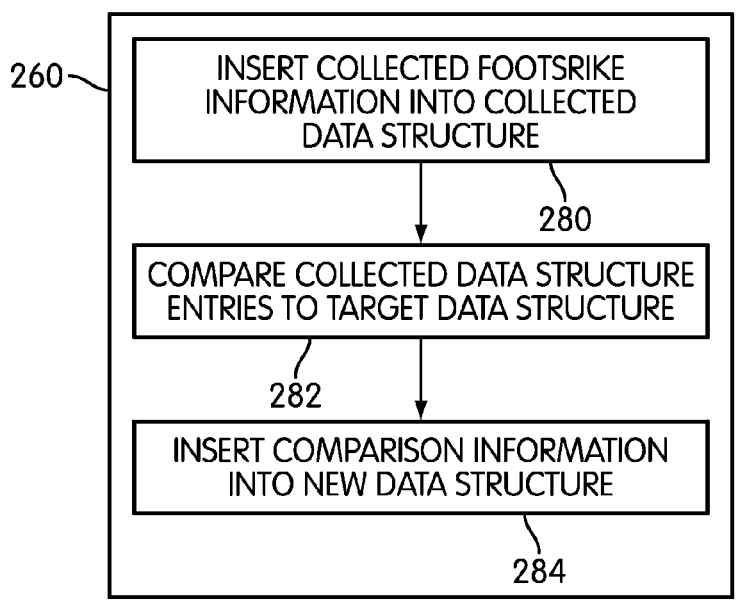
FIG. 7 is a flowchart of an embodiment of a step for comparing collected footstrike data to target footstrike data.

In step 260 of method 250 the footstrike information gathered from sensor system 107 is compared to the footstrikes of the target routine. For example, as shown in the flow chart in FIG. 7, in step 280 processor 112 preferably has inserted into a collected data structure the left and right footstrikes and the timing of those footstrikes from the routine generated by the user to be evaluated in memory module 114. Processor 112 has preferably already stored a similarly structured target data structure of left and right footstrikes and the timing of those footstrikes for the target routine in memory module 114. In step 282, processor 112 may then run an algorithm to compare the information in the target routine database with the information in the first routine database. The algorithm may be any known comparison algorithm programmed in any available computer language. For example, each entry in the data structures may be compared side-by-side for inconsistencies. Preferably, processor 112 performs this comparison on an on-going basis for real-time feedback to the user. However, in other embodiments, processor 112 may collect and store the entirety of the routine performed by the user to be evaluated prior to performing the analysis and comparison of the footstrikes. Finally, in step 284, the results of the comparison in step 282 are inserted into a new data structure. For example, only the inconsistencies may be stored, or a CORRECT or INCORRECT tag may be stored. In an alternate embodiment, the collected data structure may be tagged to note inconsistencies so that no new data structure need be created.

Figure 6:
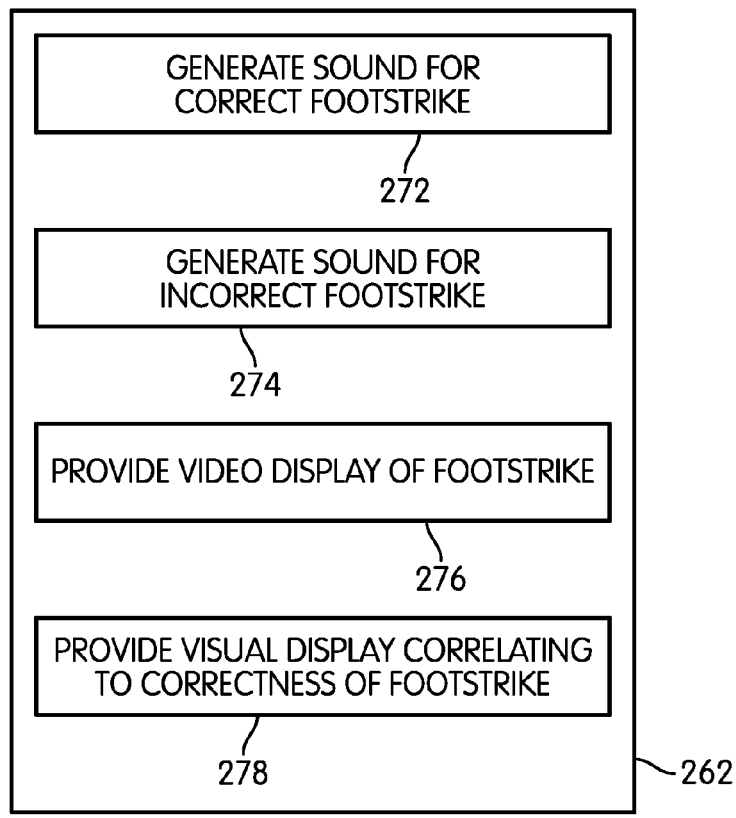
FIG. 6 is a flowchart of optional additional steps of the method of FIG. 5.

In step 262, the comparison information generated is displayed on display 118. FIG. 6 shows a flowchart of various ways in which the results may be displayed. In step 272, a sound may be generated to indicate a correct footstrike. For example, if a right foot is indicated in the target routine and a right foot is detected by sensor system 107, then a pleasant tone may sound or a voice may speak an affirmative word or phrase, such as CORRECT or GOT IT or the like. Any form of voice generation software may be used to speak the words. In step 274, a sound may be generated only to indicate an incorrect footstrike. For example, if a right footstrike is expected per the target routine and a left footstrike or no footstrike is collected by sensor system 107, then a discordant tone may sound. Alternatively, a voice may speak a negative word or phrase such as WRONG or MISSED RIGHT FOOT. In step 276, a visual representation of the footstrike may be provided on a visual display. For example, the occurrence of the footstrike in the routine generated by the user may be indicated, such as with a graphic. In another embodiment, not only the occurrence but the correctness of the footstrike may be indicated, as shown in step 278. For example, the captured footstrike may be shown as a graphic alongside a graphic for the anticipated footstrike of the target routine. The graphic selected for a correct footstrike may differ from the graphic displayed for an incorrect footstrike, such as by changing the color of the graphic or the graphic itself. For example, a green footprint may be displayed for a correct footstrike while a red footprint may be displayed for an incorrect footstrike. In another example, a circle may be displayed for a correct footstrike while an X may be displayed for an incorrect footstrike. The correctness of the footstrike may include timing of the footstrike as well as whether or not the anticipated foot (right or left) struck the surface or if the appropriate part of a foot, as determined by sensor system 107 in article of footwear 102, struck the surface at the anticipated time.

Preferably, a timing element is included in the display of footstrike information. The timing element may be expressly displayed, such as a periodic sound, expressly visually displayed, such as using a graphic or a series of graphics, or visually implied, such as by visually placing the representations of the footstrike elements at distances which indicate the temporal relationship of the footstrikes.

As will be recognized by those in the art, the order of the steps of method 250 are not necessarily sequentially as shown. In some embodiments, certain steps may be switched, some steps may occur simultaneously, or some steps may be eliminated. For example, while a user performs his or her routine, system 100 may be simultaneously capturing the footstrikes with article of footwear 102, displaying the footstrikes on display 118, analyzing the footstrikes, comparing the footstrikes with those of the target routine, and displaying the results of the comparison. In other embodiments, the entire routine may be performed before system 100 displays, analyzes, or compares the footstrikes.

Figure 8:
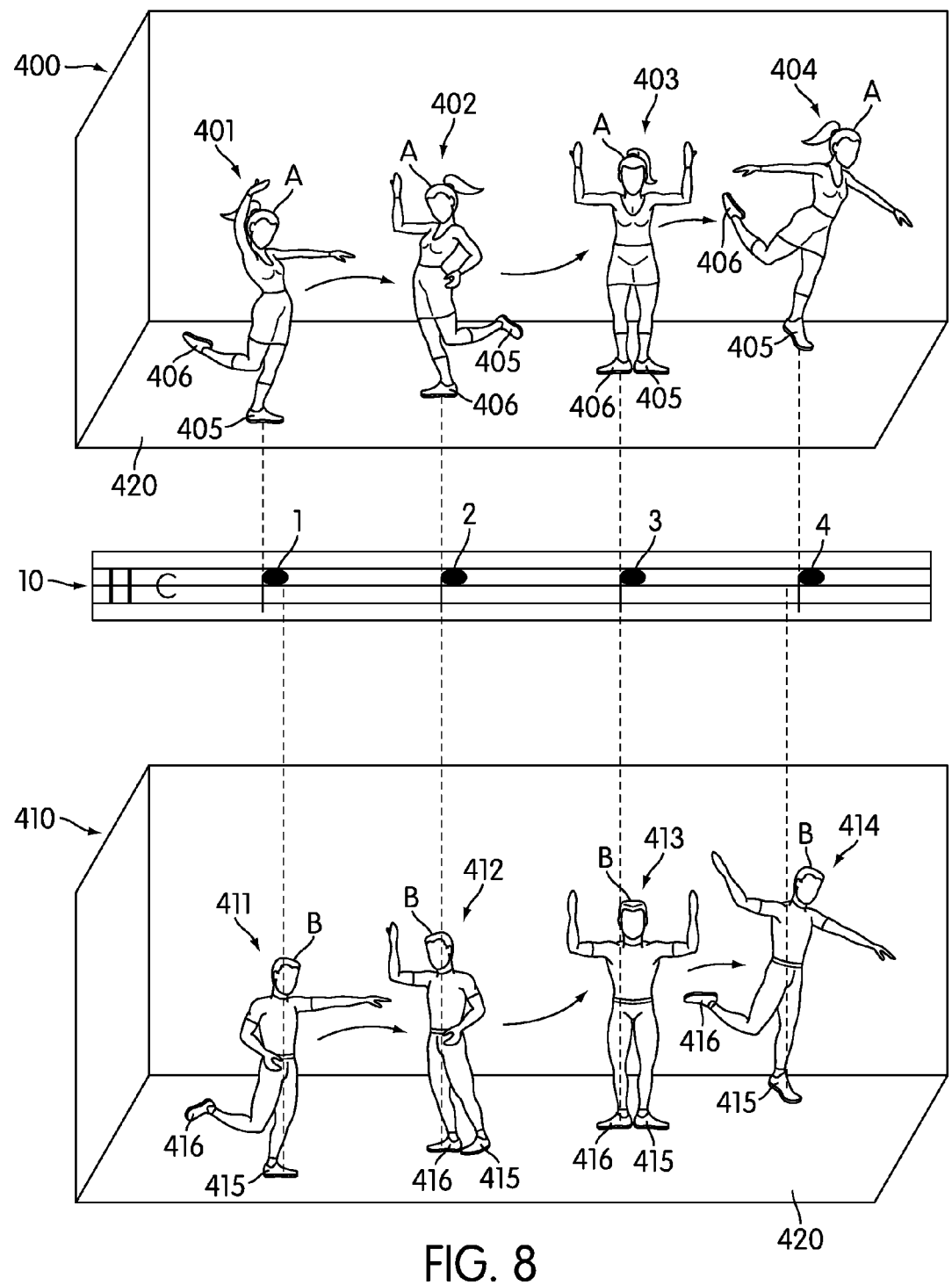
FIG. 8 is a schematic drawing of a first dancer dancing a target routine to a piece of music and a second dancer attempting to dance the same routine.

An example of method 250 is described below in conjunction with FIGS. 8-12. FIG. 8 shows a Dancer A dancing a four-step target routine 400 across a dance floor 420 to a piece of music 10, shown here as a standard drum line. The beats are indicated on the drum line as quarter notes 1, 2, 3, 4 in 4/4 time. Dancer A touches at least one of her feet to dance floor 420 per step, with each step corresponding to a beat of music 10: first step 401 corresponds to first beat 1, second step 402 corresponds to second beat 2, third step 403 corresponds to third beat 3, and fourth step 404 corresponds to fourth beat 4. While the entire body of Dancer A may be moving, only the footstrikes of a right foot wearing right foot sensor footwear 405 and a left foot wearing left foot sensor footwear 406 are captured by an evaluation system, such as system 100 discussed above, and stored in memory, such as memory module 114 discussed above, as the target routine, corresponding to step 254 of method 250.

Corresponding to step 256 of method 250, a Dancer B attempts to emulate target routine 400 by dancing a first routine 410 on the same or similar dance floor 420. The steps danced by Dancer B, first step 411, second step 412, third step 413, and fourth step 414, are meant to correspond to the steps danced by Dancer A, first step 401, second step 402, third step 403, and fourth step 404, respectively. Similar to Dancer A, while the entire body of Dancer B may be moving, only the footstrikes of a right foot wearing right foot sensor footwear 415 and a left foot wearing left foot sensor footwear 416 are captured by this embodiment of system 100 when Dancer B dances his first step 411, second step 412, third step 413, and fourth step 414 per step 258 of method 250.

Preferably, first routine 410 occurs at a later time than target routine 400, even if the delay is slight. In another embodiment, however, both Dancers A, B may be dancing simultaneously, such as in a classroom. Also, in other embodiments, multiple dancers may be evaluated according to target routine 400. For the purposes of clarity, only one evaluated dancer, Dancer B, is discussed. Similarly, while only four beats of music 10 are shown with a corresponding number of steps in target routine 400, additional beats may be danced and stored for a longer performance. However, for the sake of clarity, only the performance associated with one measure of music 10 are shown.

In step 262 of method 250, the footstrike pattern generated by Dancer B is displayed along with the results of comparing first routine 410 of Dancer B with the target routine 400 of Dancer A. FIGS. 9-12 show visual representations of target routine 400 and first routine 410 on a screen 500, such as would be found on a display such as display 118 described above. Preferably, screen 500 indicates the current beat of music 10, the footstrike patterns of target routine 400 and first routine 410, and an evaluation of first routine 410 compared with target routine 400. In this embodiment, the first column of screen 500, labeled BEAT, visually signals the current beat by placing a bar 501 over the current beat. In other embodiments, the beat may be indicated in alternate ways, such as a flashing light or group of pixels, such as on a bar which grows as time elapses, or in other graphical ways. In another embodiment, the display may scroll the images of the beats horizontally or vertically. Using such scrolling technology, the current beat and the surrounding beats may be placed in the same or similar spot on the screen so that the user does not need to shift his or her attention while performing his or her routine. In other embodiments, the current beat may be identified aurally, such as with a spoken voice counting out a measure or a drum sound.

Screen 500 includes columns "A" and "B" which correspond to Dancer A and Dancer B, respectively. Each column is preferably separated into two columns, "L" to indicate the footstrike of the left sensor footwear, 405, 415 and "R" to indicate the footstrike of the right sensor footwear 406, 416. Preferably, a simple graphical representation of the footstrike is displayed, such as an X as shown in FIGS. 9-12. However, in other embodiments, other graphics may be used to indicate a footstrike, such as a footprint, an asterisk, other simple graphics or more complicated graphics. The timing of the footstrike is also preferably indicated as being level with or offset vertically from the anticipated footstrike shown in column A. If the X in column B is aligned with the X in column A, then the footstrike in column B is timed correctly. If the X in column B is offset vertically above the X in column A, then the footstrike is early. If the X in column B is offset vertically below the X in column A, then the footstrike of Dancer B is late.

As shown in FIGS. 9-12, target routine 400, shown in column A of screen 500, specifies only a footstrike with an X and not the location of the footstrike or the part of the foot which strikes dance floor 420. Preferably, however, the timing of the footstrike is shown in the center of the box to indicate hitting the beat with appropriate timing.

The final column of screen 500, labeled RESULT shows an evaluation of the footstrikes of Dancer B. Preferably, the RESULT column is divided into two parts, one to evaluate whether or not the foot fall is appropriate. For example, if the target routine requires a strike of the right foot, this box indicates whether or not the right foot and only the right foot of Dancer B strikes. Any deviation, such as no strike of the right foot or the strike of both feet would yield and INCORRECT result. The timing of Dancer B is evaluated in the second box. If the strike hits with the target routine, the timing is indicated as GOOD. If the strike hits before the strike of the target routine, the timing is indicated as EARLY. If the strike hits after the strike of the target routine, the strike in evaluated as LATE.

In other embodiments, the screen may use different terms or alternate ways to evaluate the performance of Dancer B. For example, the evaluation may be more complicated, with more precise information being displayed about the timing of the footstrikes of Dancer B. In another example, a symbol may be used to represent good, early, and/or late timing. In another embodiment, the graphical interface may have an entirely different appearance, such as by streaming the information horizontally, showing only one beat at a time, or the present beat and one future beat, or any number of additional configurations.

In this embodiment, Dancer A dances her entire target routine 400 prior to dancer B dancing his first routine 410 so that all four footstrikes, those of first step 401, second step 402, third step 403, and fourth step 404, are shown on the screen at once. In another embodiment, in which Dancer A may dance simultaneously with or only slightly ahead of Dancer B, target routine 400 may be programmed, or target routine 400 may be too long to display all at once on a single screen. In such a case, preferably the footstrikes of Dancer A, the visual indications of first step 401, second step 402, third step 403, and fourth step 404, would scroll on the screen so that Dancer B may follow along. The footstrike pattern of Dancer A is detected by sensor system 107, transmitted to processor 112 for interpretation and data organization, and stored in memory module 114.

In step 256 of method 250 shown in FIG. 5, Dancer B begins his first routine 410 by hitting first step 411. As Dancer B's right foot strikes dance floor 420, the sensors in right foot article of footwear 415 detect the impact and transmit the impact information to an evaluation module, such as evaluation module 104 discussed above. In step 258 of method 250, the evaluation system captures the footstrike of Dancer B and, per step 260, displays the footstrike of first step 411 visually on screen 500, as shown in FIG. 9. Therefore, in column labeled B, a visual representation of first step 411 appears as an X. As shown, Dancer B strikes the correct foot on floor 420, but is late in doing so. Therefore, the X in column B is offset vertically below the X for beat 1 in column A. Corresponding to step 258 of method 250, processor 112 compares this footstrike with step 401 of target routine 400, and determines that the footfall is correct while the timing of first step 411 is late. In the RESULT column on screen 500, the foot fall is labeled CORRECT and the timing is labeled LATE.

Dancer B then dances second step 412. As shown in FIG. 8, Dancer B incorrectly plants both feet on the floor, but his timing is correct. When Dancer B's feet impact dance floor 420, the sensors in right foot article of footwear 415 and left foot article of footwear 416 detect the impact sand transmit the impact information to the evaluation module. In step 258 of method 250, the evaluation system captures the footstrike of Dancer B and, per step 260, displays the footstrike of second step 412 visually on screen 500. As shown in FIG. 10, column B of screen 500 displays two Xs which appear aligned with the single X shown in column A to represent Dancer A's second step 402. Processor 112 compares this footstrike from second step 412 danced by Dancer B with the footstrike from second step 402 danced by Dancer A, and determines that the foot fall of Dancer B is incorrect while the timing is correct. In the RESULT column of screen 500, the foot fall is labeled INCORRECT and the timing is labeled CORRECT.

Dancer B then dances third step 413. As shown in FIG. 8, Dancer B again plants both feet on floor 420, hitting beat 3 at the same time as Dancer A plants her feet on floor 420 in third step 403. Footwear 415 and 416 detect and transmit the footstrikes of Dancer B to the evaluation module. In column B of screen 500, two Xs appear aligned with the two Xs in column A. Processor 112 compares the footstrike of Dancer B's third step 413 with the footstrike of Dancer A's third step 403, and determines that both foot fall and timing are correct. Therefore, in the RESULT column on screen 500, the foot fall is labeled CORRECT and the timing is labeled CORRECT.

Finally, Dancer B dances his fourth step 414. As shown in FIG. 8, Dancer B correctly puts only his right foot on floor 420 but hits beat 4 earlier than Dancer A. As Dancer B's right foot strikes dance floor 420, the sensors in right foot article of footwear 415 detect the impact and transmit the impact information to the evaluation module. The evaluation module captures the footstrike of Dancer B and displays the footstrike of fourth step 414 visually on screen 500. As shown in FIG. 12, a single X is displayed in column B on screen 500 to represent fourth step 414, but offsets the X vertically above the X in column A which represents Dancer A's fourth step 404. This vertical offset shows that fourth step 414 occurred earlier than fourth step 404. Processor 112 compares Dancer B's fourth step 414 with Dancer A's fourth step 404 and determines that Dancer B's foot fall is correct while the timing is early. Therefore, screen 500 shows in the RESULT column that the foot fall is CORRECT while the timing is LATE.

Preferably, the comparison of the performance of Dancer B with that of Dancer A is summarized in a final screen, as shown in FIG. 13. In this embodiment, Dancer B's correct footfalls and correct timing hits are shown as a fraction of the total number of footfalls and timing hits danced by Dancer A. Here, Dancer A danced four (4) steps, so there are four (4) possible correct footfalls. Dancer B's footfalls were correct only three (3) times, so the screen displays 3/4 and 75% as Dancer B's score or comparison metric. Dancer B's timing was correct only twice, so the screen displays 2/4 and 50% as Dancer B's score or comparison metric. It will be understood that in other embodiments, the score or comparison metric may take other forms, such as a percentage, a score derived from the raw data, such as a performance scale from 1-10, association with a category such as ADEQUATE, GOOD, PERFECT, or the like, or any other type of scoring system desired.

Preferably, an evaluation system such as system 100 is capable of storing historical performance data for a user. Over time, it is anticipated that a dancer will improve as he or she learns the steps and timing of the new dance. In one embodiment, the results of a dancer's performance, such as the score, performance metric or complete footstrike pattern, of a particular dancer's session are stored in memory for long-term evaluation. Because Dancer B has performed the target routine danced by Dancer A only once, no historical data is available, and screen 500 displays a notice to that effect.

Figure 14:
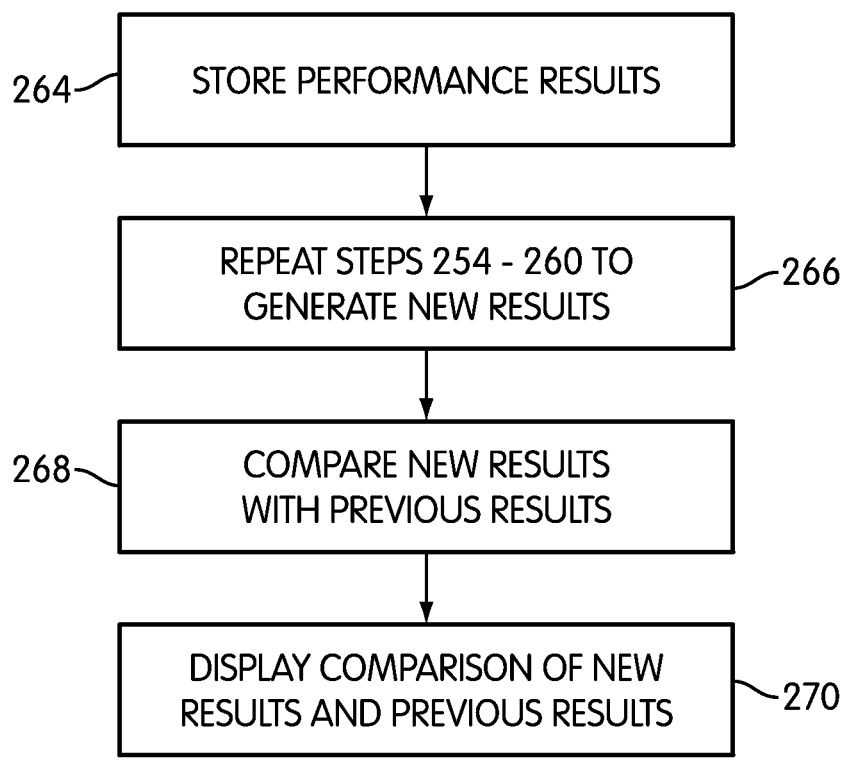
FIG. 14 is a flowchart of optional additional steps of the method of FIG. 5.

FIG. 14 shows various additional steps which may be included with method 250 as shown in FIG. 5 in order to provide this optional progressive evaluation capability to system 100. In step 264, the performance results as generated by processor 112 in step 260 of evaluation method 250 are stored, such as in memory module 114 for future reference. In step 266, steps 254-260 of method 250 are repeated so that a second routine is performed by the evaluated dancer, such as Dancer B, and evaluation results as compared to the target routine are generated. In step 268 the performance results for the second routine are compared with the performance results for the first routine. For example, the evaluation system may compare the total number of late or early footstrikes in the first routine with the total number of late or early footstrikes in the second routine. Alternatively, the evaluation system may compare the total number of correctly timed footstrikes in the first routine with the total number of incorrectly timed footstrikes in the second routine. In step 270 the comparison of the results of the first routine and the second routine are displayed. For example, a screen may show the progress or lack or progress of the evaluated dancer by indicated the increase in correct footstrikes or the decrease in the number of correct footstrikes.

Figure 15:
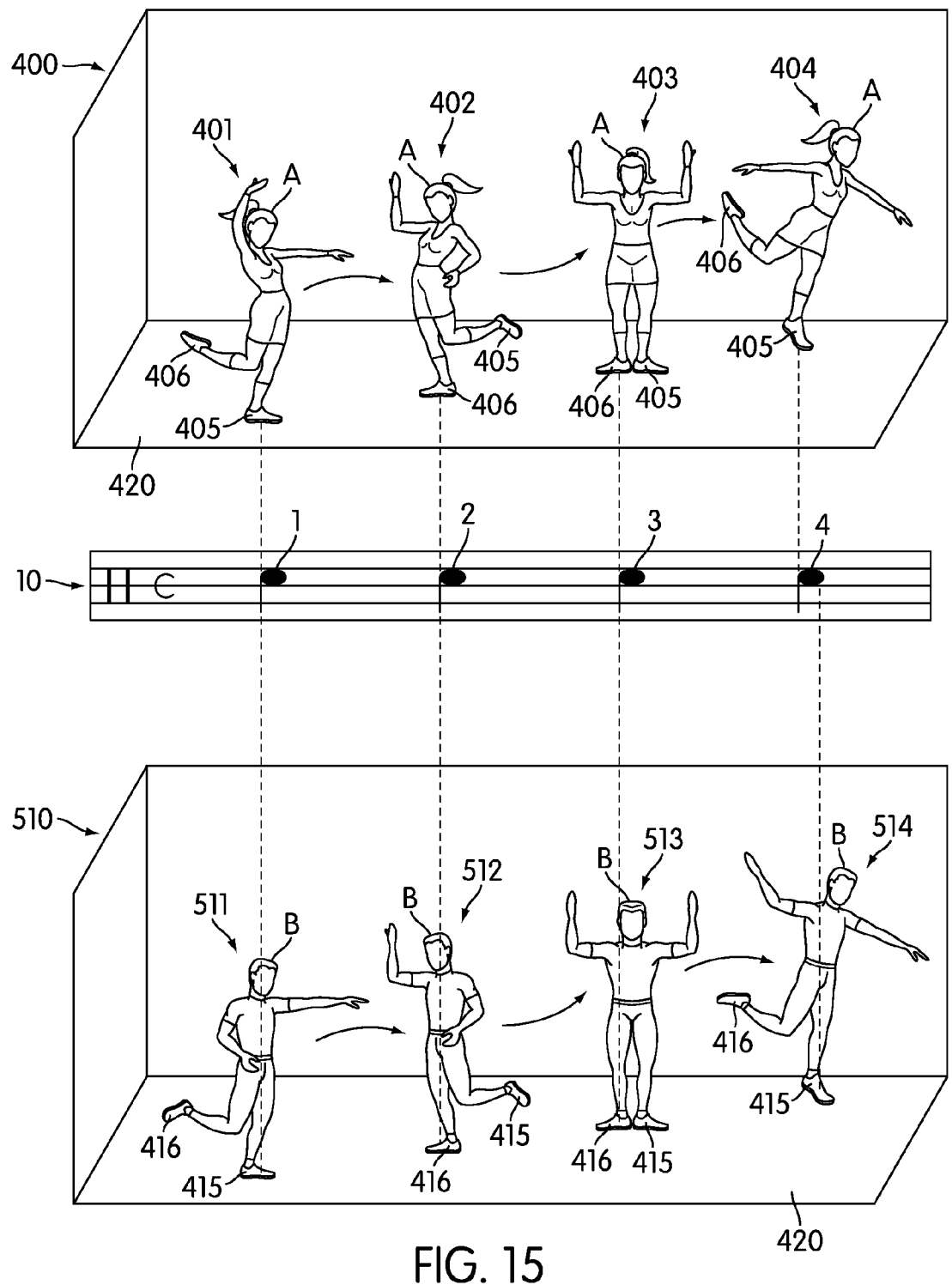
FIG. 15 is a schematic drawing of the first dancer of FIG. 8 dancing the same target routine at a later time and the second dancer attempting once again to dance the target routine.

FIG. 15 shows Dancer A once again dancing her target routine 400 to music 10, as also shown in FIG. 8. Dancer B, however, dances a second routine 510, attempting once again accurately to emulate the footstrike pattern of Dancer A. Therefore, second routine 510 is an iteration of first routine 410 as danced by Dancer B, with Dancer B attempting to correct the mistakes of first routine 410 so that his routine more closely resembles Dancer A's target routine 400. Each footstrike is detected by right foot article of footwear 415 or left foot article of footwear 416 for transmission to and interpretation by the evaluation module (not shown) for comparison with Dancer A's target routine 400.

Second routine 510 includes a first step 511, a second step 512, a third step 513, and a fourth step 514. In second routine 510, Dancer B's first step 511 corresponds precisely with Dancer A's first step 401. Therefore, as shown in FIG. 16, the Xs indicating both steps 511 and 401 align on screen 500. Further, after processor 112 compares Dancer B's first step 511 with Dancer A's first step 401, screen 500 indicates CORRECT for the foot fall and CORRECT for the timing. Dancer B's second step 512 and third step 513 also correspond accurately with Dancer A's second step 402 and third step 403, respectively. As shown in FIGS. 17 and 18, the Xs indicating both steps 511 and 401 align on screen 500, as do the Xs indicating steps 513 and 403. After processor 112 compares Dancer B's second step 512 with Dancer A's second step 402 and Dancer B's third step 513 with Dancer A's third step 403, screen 500 indicates CORRECT for the foot fall and CORRECT for the timing for both beats 2 and 3.

While Dancer B has improved overall, fourth step 514 does not accurately match Dancer A's fourth step 404. Dancer B hits step 514 on the correct foot, but late. Therefore, on screen 500 as shown in FIG. 19, the X indicating Dancer B's step 514 is offset vertically below the X indicating Dancer A's step 404. Further, when processor 112 has compared Dancer B's fourth step with Dancer A's fourth step 404, screen 500 indicates CORRECT for the footfall but LATE for the timing.

FIG. 20 shows a summary screen of the performance results for Dancer B's second routine 510. In this embodiment, Dancer B's correct footfalls and correct timing hits are shown as a fraction of the total number of footfalls and timing hits danced by Dancer A, although other scoring metrics may be used in other embodiments, as discussed above. Here, Dancer A danced four (4) steps, so there are four (4) possible correct footfalls. Dancer B's footfalls were correct all four (4) times, so screen 500 displays 4/4 and 100% as Dancer B's score or comparison metric. Dancer B's timing matched Dancer A's timing three (3) times, so the screen displays 4/4 and 100% as Dancer B's score or comparison metric. Additionally, because the system has a previous performance metric stored for Dancer B, the system can compare the old and new performance metrics to develop a progress metric. As shown in FIG. 20, the screen simply displays IMPROVED FOOTFALL and IMPROVED TIMING, although in other embodiments, additional or different information could be displayed to indicate to a user how well he or she is learning the activity.

Figure 21:
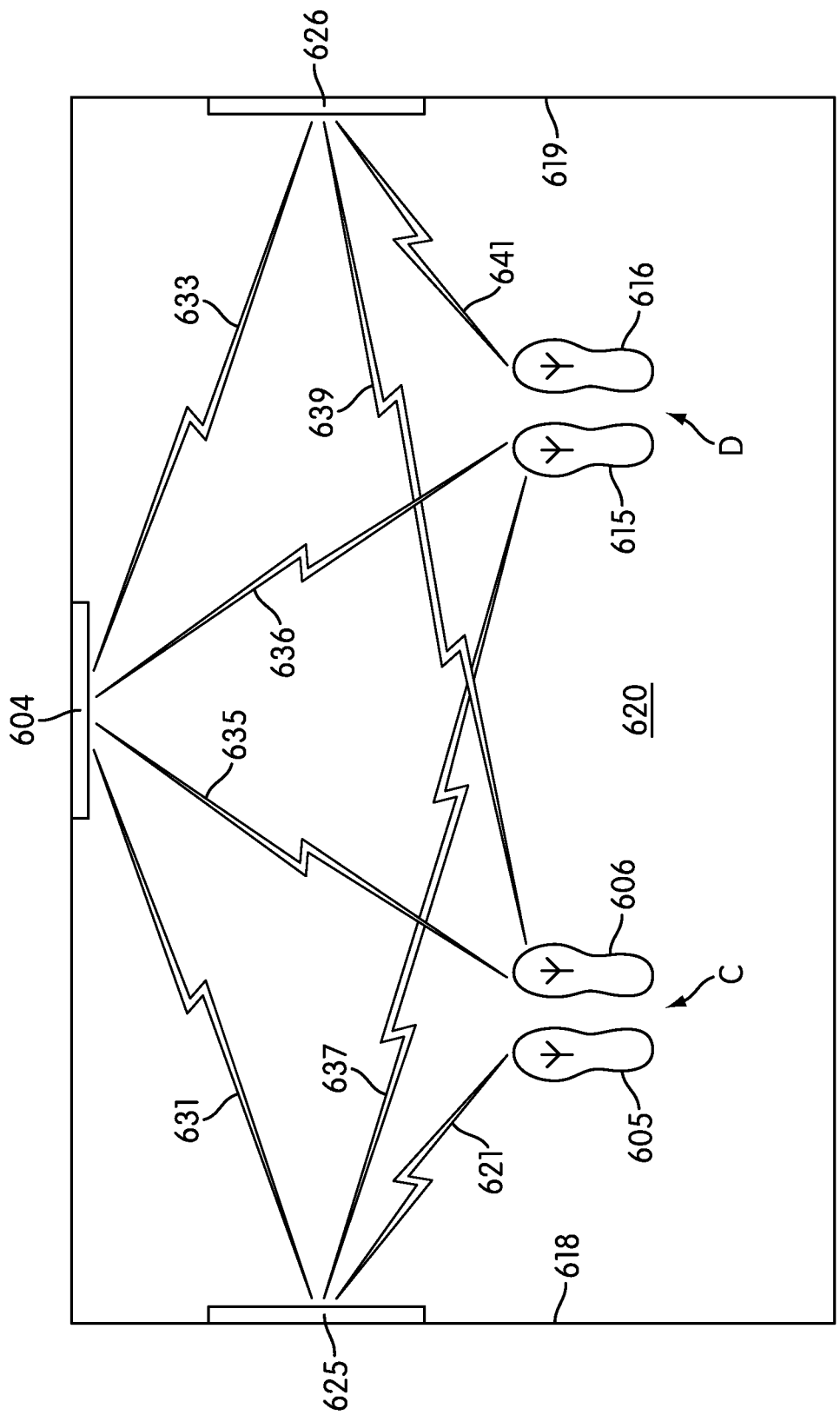
FIG. 21 is a schematic view showing another embodiment of the evaluation system for use with multiple dancers.

Optionally, system 100 may be capable of noting the performances of multiple users at once. As shown in FIG. 21, two dancers, C and D, are performing a routine simultaneously on a dance floor 620. While only two dancers are shown and discussed, any number of dancers are contemplated. First dancer C is provided with a right foot sensor article 606 and a left foot sensor article 605. Similarly, second dancer D is provided with right foot sensor article 616 and left foot sensor article 616. An evaluation module 604, similar to evaluation module 104 described above, is provided to receive and evaluate footstrike information from first dancer C and second dancer D. Preferably, evaluation module 604 is configured to receive wireless signals from articles 605, 606, 615, and 616. The signals may be any type of wireless signal known in the art, such as an RF signal, a Bluetooth signal, or an optical signal. Evaluation module 604 is preferably centrally located alone on dance floor 620 or along one wall adjacent to dance floor 620.

Preferably evaluation module 604 determines the location of first dancer C and second dancer D on dance floor 620 using triangulation of RF signals. To do so, multiple transceivers for the signals generated by articles 605, 606, 615, and 616 are provided. While any number of transceivers may be provided, preferably, two transceivers 625 and 626 are provided in addition to evaluation module 604. Transceivers 625 and 626 preferably do not include storage or evaluation capabilities, but receive, tag, and retransmit signals to evaluation module 604. Transceivers 625 and 626 are preferably positioned to maximize the distance between transceivers 625 and 626 and evaluation module 604 while still allowing each of transceivers 625 and 626 and evaluation module 604 to maintain an unobstructed "view" of each dancer C and D. For example, an unobstructed view may include line of sight for optical systems and lack of interference-causing obstructions, such as metal poles or other wireless systems, for RF systems. By way of example only, first transceiver 625 is placed on a left wall 618, second transceiver 626 is placed on a right wall 619, and evaluation module 604 is positioned between first transceiver 625 and second transceiver 626.

In operation, each dancer C and D performs a routine on dance floor 620. Each dancer C and D or each of articles 605, 606, 615, and 616 transmits a signal to each of evaluation module 604 and transceivers 625 and 626. For simplicity, each dancer C and D transmits a single signal to each of evaluation module 604, first transceiver 625, and second transceiver. For example, first dancer C is communicatively connected to evaluation module 604 via first link 635, to first transceiver 625 via second link 621, and to second transceiver 626 via third link 639. Similarly, second dancer D is communicatively connected to evaluation module 604 via fourth link 636, to first transceiver 625 via fifth link 637, and to second transceiver 626 via sixth link 641.

First transceiver 625 receives a signal from first dancer C via second link 621, tags the signal with a unique identifier using known protocols, and re-transmits the signal to evaluation module 604 via seventh link 631. First transceiver 625 also receives a signal from second dancer D via fifth link 637, tags the signal with a unique identifier using known protocols, and re-transmits the signal to evaluation module via seventh link 631. Evaluation module 604 receives and stores in a data structure the signals from first transceiver 625 and second transceiver 626. The data structure may be any type known in the art, such as a database.

Similarly and preferably simultaneously, second transceiver 626 receives a signal from first dancer C via third link 639, tags the signal with a unique identifier using known protocols, and re-transmits the signal to evaluation module 604 via eighth link 633. Second transceiver 626 receives a signal from second dancer D via sixth link 641, tags the signal with a unique identifier using known protocols, and re-transmits the signal to evaluation module 604 via eighth link 633. Evaluation module 604 receives and stores in a data structure the signals from first transceiver 625 and second transceiver 626.

Similarly, and preferably simultaneously or substantially simultaneously, evaluation module 604 receives a signal directly from first dancer C via first link 635. Evaluation module 604 tags the signal with a unique identifier using known protocols and stores the signal in a data structure.

Evaluation module 604 is preferably programmed with a triangulation algorithm capable of determining the location of dancers C and D. The triangulation algorithm may be any triangulation algorithm known in the art. In this manner, evaluation module 604 may determine and evaluate not just the footstrikes generated by dancers C and D, but also calculate their position on dance floor 620 and relative to each other. Such a system is particularly suited for choreographing, teaching, and evaluating routines with multiple members, such as cheerleaders, dance teams, or dance performances.

Although a live dance class is shown and discussed above with respect to FIGS. 8-20, the inventive evaluation system may be used for additional activities. For example, a user with a home video gaming system or computer may be provided with components of a system such as system 100, such as an article of footwear with sensors and a communication link, a receiver for communicating with the article of footwear, and software to run the data interpretation and comparison modules. The user may also be provided with a number of target routines in the software and related video and music. For example, the user may be provided with video of the dance routine of a popular music star and the footstrike pattern. The user may then learn the dance routine and be able to evaluate his or her progress in the privacy of his or her own home. Alternatively, the user may be provided with a demonstration of a yoga posture, tai chi motions, martial arts movements, or the like.

Figure 22:
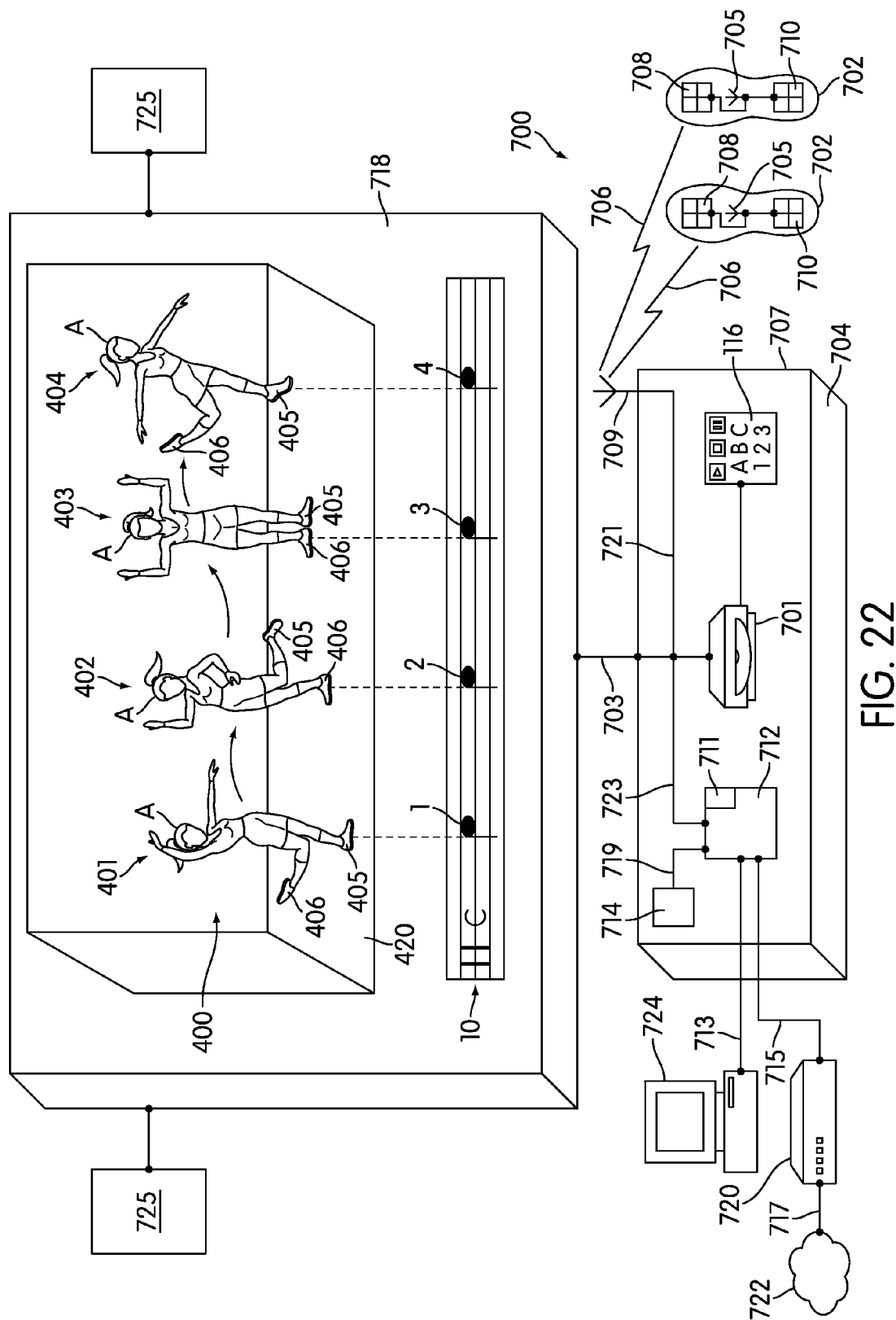
FIG. 22 is a schematic view showing a an embodiment of a system to display a target routine and to collect, evaluate, and store user footstrike information.

Such a system 700 is shown in FIG. 22. A user is provided with sensor-rich articles of footwear 702 which are similar to article of footwear 102 described above. Each article preferably includes a forefoot array 708 of sensors a rearfoot array 710 of sensors linked to a transmitter 705. The user may be provided with one or two articles 102.

Transmitter 705 is communicatively linked to an evaluation module 704. Evaluation module 704 is similar to evaluation module 104 described above in that evaluation module 704 preferably includes within a housing 707 a processor 712 including a timing circuit or clock 711 connected via a link 719 to a memory module 714 capable of storing target and collected information. Evaluation module 704 also preferably includes a transceiver 709 communicatively linked to articles of footwear 702 via link 706 and to processor 712 via link 721. While shown as a wireless link, link 706 may also be a wireline link.

Processor 712 is also connected via a link 723 to a target routine input unit 701. Target routine input unit 701 is preferably an optical or magnetic drive, such as a CD or DVD drive, floppy disk drive, video cassette reader, memory card or stick reader, or the like. Target routine input unit 701 is preferably operated by the user via an input device 116, such as a keyboard, button panel, touch screen, microphone, remote control, or the like mounted onto a face of housing 707. User may upload to processor 712 the target routine via target routine input unit 701. The target routine is preferably stored on a DVD, but also may be stored on a CD, floppy disk, video cassette, memory stick, or the like. The target routine preferably includes an audio/visual file of a dancer A performing the routine, a visual representation 10 of the beats of the music, and a data structure of a footstrike pattern generated by dancer A. The data structure is preferably transmitted and stored in memory module 714, while the audio/visual file of dancer A is preferably streamed or otherwise transmitted directly from target routine input device 701 to a display 718 via a link 703. As discussed above with respect to display 118, display 718 may be any type of display known in the art. Display 718 includes not only a screen for visual display, but also at least one audio-generating device, such as left and right speakers 725.

As described above with respect to FIGS. 5-20, dancer A performs a target routine that the user (not shown) attempts to emulate. Articles 702 capture footstrike information and transmit that information to evaluation module 704. The footstrike information is communicated to processor 712, which may store the footstrike information in memory module 714. Optionally, the footstrike information may be stored in an external device 724 via a link 713. External device 724 may be a computer with memory, an optical disk, a magnetic disk or tape, a memory stick, or the like.

Processor 712 evaluates the footstrike information collected from articles 702 as described above with respect to FIGS. 5-20. While not shown in this embodiment, in other embodiments, display 718 may provide a scrolling visual representation of the footstrike information generated by articles 702, similar to the screen shots shown in FIGS. 6-9. The user may perform the routine multiple times, with the information from each iteration stored in memory module 714 or external device 724. External device 724 may also act as a back-up system for memory module 714.

Additionally, the evaluation of the footstrikes generated by articles 702 or even the footstrikes themselves may be transmitted from processor 712 to a communications network 722. For example, communications network 722 may be linked to a modem 720 via a communications link 717. In turn, modem is linked to processor 712 via link 715. Modem 720 may be any type of digital or analog communications tool, such as a stand-alone unit, integrated card or device within housing 707, or part of external device 724. Communications network 722 may be any type of network known in the art, but is preferably the Internet.

Figure 23:
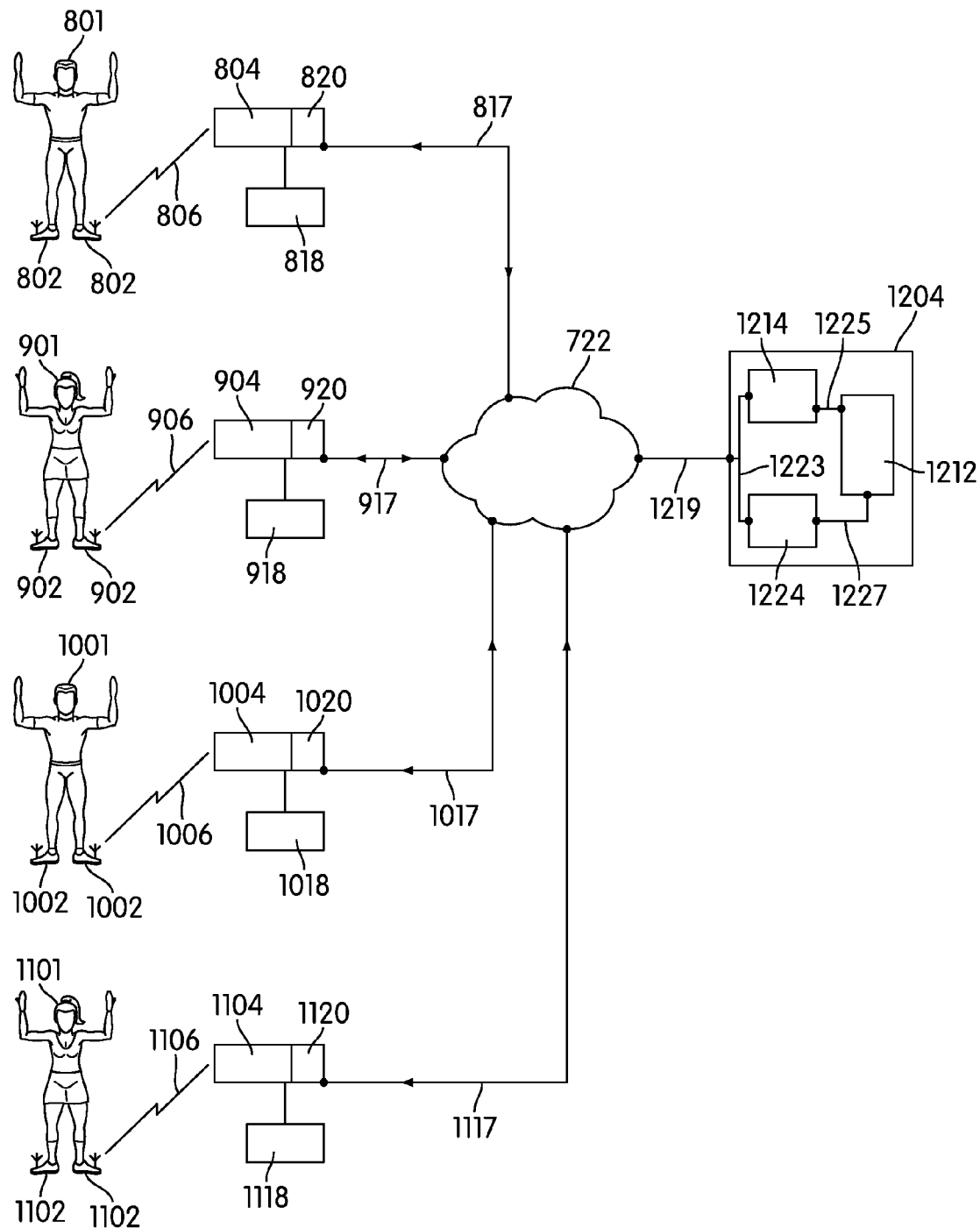
FIG. 23 is a schematic view of an embodiment of a footstrike evaluation system that allows multiple users at multiple locations to compare results.

Transmission of performance data to communications network 722 may be used to back up information or other similar uses, but is preferably used to allow several users to compare performance data. Online performance comparisons and competitions are known, such as the Nike+iPod® system, or the system described in U.S. Pat. No. 7,072,789, which is incorporated herein by reference. In the embodiment shown in FIG. 23, four users 801, 901, 1001, and 1101 are each provided with a system 800, 900, 1000, 1100. Each system 800, 900, 1000, and 1100, is similar to system 700. For example, user 801 is provided with sensor articles 802 which are linked to an evaluation module 804 via link 806. Evaluation module 804 is connected to a display 818 and a modem 820. Modem 820 transmits performance data to communications network 722 via a link 817. Similarly, user 901 is provided with sensor articles 902 which are linked to an evaluation module 904 via link 906. Evaluation module 904 is connected to a display 918 and a modem 920. Modem 920 transmits performance data to communications network 722 via a link 917. User 1001 is provided with sensor articles 1002 which are linked to an evaluation module 1004 via link 1006. Evaluation module 1004 is connected to a display 1018 and a modem 1020. Modem 1020 transmits performance data to communications network 722 via a link 1017. User 1101 is provided with sensor articles 1102 which are linked to an evaluation module 1104 via link 1106. Evaluation module 1104 is connected to a display 1118 and a modem 1120. Modem 1120 transmits performance data to communications network 722 via a link 1117.

Also connected to communications network 722 via a link 1219 is a master evaluation module 1204. Master evaluation module 1204 includes a processor 1212 linked to a memory module 1214 via a link 1225. Preferably, memory module 1214, which may be any type of information storage device known in the art, provides significant capacity so that any number of users may participate in an online comparison or competition.

Master evaluation module 1204 also preferably includes a website 1224 for users 801, 901, 1001, and 1101 to interact directly with evaluation module 1204 and/or each other. In the context of this invention, "website" may be any type of HTML or XML program accessible by any user via communications network 722. Website 1224 is linked to processor 1212 via a link 1227 and to communications network 722 via links 1223 and 1219.

In operation, master evaluation module 1204 may gather performance data, such as a footstrike and timing pattern, for all users 801, 901, 1001, and 1101 and compare the data to a target routine stored in memory module 1214. Preferably, however, master evaluation module 1204 gathers only the evaluation performance information, such as the information displayed in FIG. 13, produced by each evaluation module 804, 904, 1004, and 1104, such as is produced in step 260 of the method shown in FIG. 5. This expedites the comparison of performances between users 801, 901, 1001, and 1101. Processor 1212 then compares the evaluated performance information for all users and ranks the users. For example, a "winner" may be chosen by determining which user 801, 901, 1001, and 1101 has performed closest to the target routine based upon any desired metric, including but not limited to the total number of correct footstrikes, the highest percentage of correct footstrikes, the lowest number of incorrect footstrikes, etc. Similarly, all users may be ranked according to the same metrics, with the performance closest to the target routine ranked "1", the next closest ranked "2", etc. In one embodiment, memory module 1214 stores these rankings and adjusts the rankings over time as performances change over time.

Figure 24:
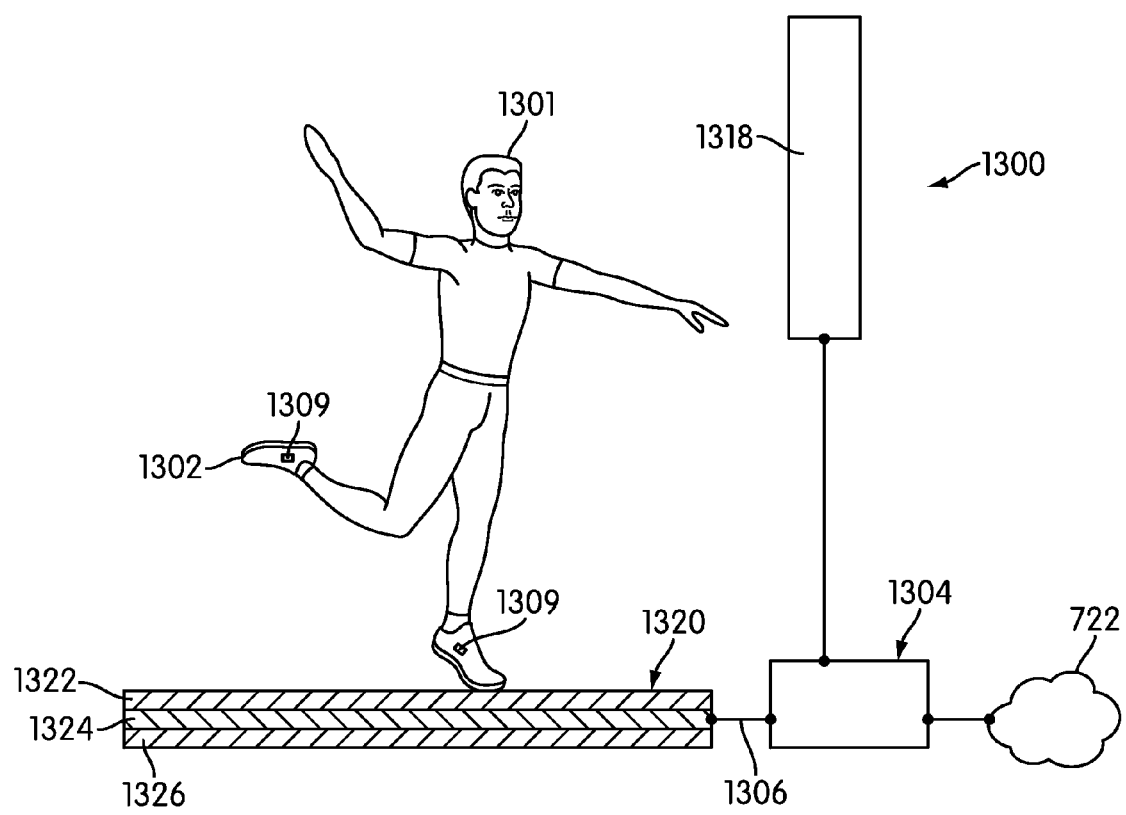
FIG. 24 is a schematic view of an embodiment of a footstrike evaluation system incorporating a sensor-rich mat and sensor-rich articles of footwear.

In another embodiment, the system provided to each user may incorporate additional sensor elements other than those placed on the user, such as those in the sensor articles of footwear. FIG. 24 shows a system 1300 having an evaluation module 1304 linked to a display and, optionally, a communications network 722 such as the Internet. System 1300 incorporates a sensor-rich mat 1320 used in conjunction with a sensor article of footwear 1302. In this embodiment, articles 1302 preferably do not communicate directly with evaluation module 1304, similar to the evaluation modules discussed above. Instead, mat 1320 is communicatively linked to evaluation module 1304 via link 1306.

Figure 25:
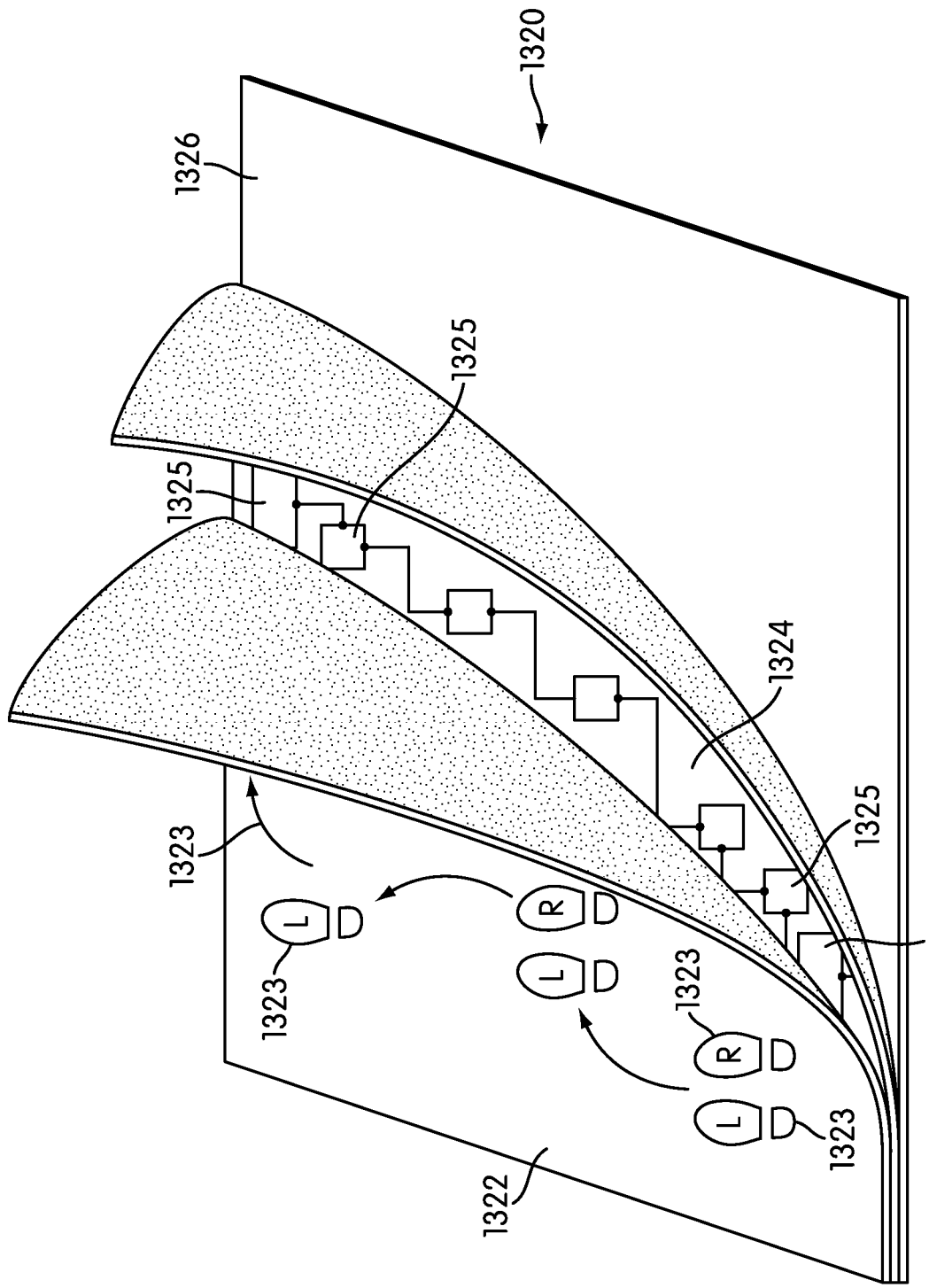
FIG. 25 is a schematic view of an embodiment of the sensor-rich mat of FIG. 24.

As shown in FIGS. 24 and 25, mat preferably includes several layers, in this embodiment, three layers. In other embodiments, however, mat 1320 may include any number of layers, including only a single layer. A first layer 1322 is positioned so that a user 1301 performs his or her routine on first layer 1322. First layer 1322 is therefore, preferably made from a durable material capable of withstanding substantial wear over time while still allowing user 1301 to move freely. For example, first layer 1322 may be made from rubber, vinyl, or similar synthetic materials. Also, as shown in FIG. 25, first layer 1322 is optionally printed with a conventional dance pattern 1323. Dance pattern 1323 is a guide to user 1301 and shows where to position the feet and arrows indicating how to move from one position to the next. Dance pattern 1323 may be places on first layer using any conventional printing technique, such as ink jet printing or embossing.

A second layer 1324 is positioned adjacent to and substantially underneath first layer 1322. Second layer 1324 includes a plurality of sensors 1325 electrically or optically connected together, such as serially or in parallel. Sensors 1325 may be powered by batteries, by connection to an electrical outlet, or via evaluation module 1304. While sensors 1325 may be any type of sensor, preferably sensor 1325 are configured to generate a signal only when in proximity to sensor 1309 on article 1302. For example, sensors 1325 may be magnetic sensors, so that a signal is generated when magnetic sensor 1309 is brought within a minimum distance to at least one of sensors 1325. Using a combination of sensor 1309 in article 1302 and sensors 1325 in mat 1320 allows for a more precise reading of the footstrike than if either sensor were used alone, as information from both sensors are used in conjunction to determine the timing and location of the footstrike. Additionally, as a plurality of sensors 1325 are positioned in mat 1320, each sensor 1325 may be provided with a unique identifier so that the location of the footstrike may be accurately measured.

A third or bottom layer 1326 is positioned adjacent to and substantially underneath second layer 1324. Third layer 1326 preferably contacts a floor or other stable and substantially flat surface. Third layer 1326 preferably provides cushioning to absorb the impact of the footstrikes of user 1301 and traction against the floor or surface. For example, third layer 1326 may be made from rubber, foam, or similar materials.

As will be appreciated, the systems disclosed herein may be used for many different activities, from learning new athletic moves, to friendly competitions between users, to assisting judges in assessing technical performances in sporting events such as dance competitions, gymnastics, or skating.

It will be understood that mat 1320 is not limited to a dancing mat. Mat 1320 may also be used for a yoga mat, with hand and feet positions printed thereupon, a wrestling mat, a tumbling or gymnastics mat, or the like.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

What is claimed is:

1. A system for evaluating a performance of a footwork-based activity, the system comprising:
    a sensor system including a first sensor disposed in a first article of footwear and a second sensor disposed in a second article of footwear;
    an evaluation module including a processor configured to communicate with the first sensor and the second sensor;
    a target routine comprising a first set of footstrike data received from the first sensor, the target routine being accessible by the processor, wherein the target routine is associated with a first user wearing the first article of footwear;
    an evaluation routine comprising a second set of footstrike data received from the second sensor, the evaluation routine being accessible by the processor, wherein the evaluation routine is associated with a second user wearing the second article of footwear;
    wherein the evaluation module is configured to generate evaluation information comparing the evaluation routine to the target routine; and
    wherein the first set of footstrike data and the second set of footstrike data each comprise a plurality of left and right footstrikes associated with a timing between successive footstrikes.

2. The system according to claim 1, wherein at least a portion of the plurality of left and right footstrikes are repetitive such that the timing between successive footstrikes is periodic.

3. The system according to claim 1, wherein the evaluation information includes a graphical comparison of the first set of footstrike data and the second set of footstrike data.

4. The system according to claim 1, wherein the footwork-based activity is running; and wherein the first set of footstrike data and the second set of footstrike data are associated with running a predetermined distance.

5. The system according to claim 1, wherein the footwork-based activity is dancing.

6. The system according to claim 1, wherein the evaluation module is configured to generate evaluation information comparing the evaluation routine to the target routine in real-time.

7. The system according to claim 1, wherein the evaluation module further comprises a memory module.

8. The system according to claim 7, wherein at least one of the target routine and the evaluation routine is stored in the memory module.

9. The system according to claim 8, wherein the first set of footstrike data, the second set of footstrike data, and the evaluation information are stored in the memory module.

* * * * *